United States Patent
Chang

(10) Patent No.: US 7,498,301 B2
(45) Date of Patent: Mar. 3, 2009

(54) COMPOSITION CONTAINING DIPEPTIDE OF HISTIDINE AND ALANINE FOR REDUCING URIC ACID AND METHOD FOR REDUCING URIC ACID USING THE DIPEPTIDE

(75) Inventor: William T. H. Chang, Taipei (TW)

(73) Assignee: Lytone Enterprise, Inc., Taipei (TW)

( * ) Notice: Subject to any disclaimer, the term of this patent is extended or adjusted under 35 U.S.C. 154(b) by 0 days.

(21) Appl. No.: 11/644,336

(22) Filed: Dec. 22, 2006

(65) Prior Publication Data

US 2007/0099846 A1    May 3, 2007

Related U.S. Application Data

(62) Division of application No. 10/449,053, filed on May 30, 2003, now abandoned.

(51) Int. Cl.
*A61K 38/00* (2006.01)
*A61K 51/00* (2006.01)
(52) U.S. Cl. ............................. 514/9; 530/300; 424/1.69
(58) Field of Classification Search .................. 514/19; 530/300; 424/1.69
See application file for complete search history.

(56) References Cited

U.S. PATENT DOCUMENTS

| 6,169,083 B1 | 1/2001 | Hirano et al. |
| 6,190,694 B1 | 2/2001 | Mizushima |
| 6,310,188 B1 | 10/2001 | Mukherjee |
| 2002/0103244 A1 | 8/2002 | Matahira et al. |
| 2002/0137713 A1 | 9/2002 | Kapeller-Libermann |
| 2003/0199446 A1 | 10/2003 | Bunger et al. |

FOREIGN PATENT DOCUMENTS

| CN | 1356103 | 10/2001 |
| JP | 9-20660 | 1/1997 |
| JP | 2002-338473 | 11/2002 |

OTHER PUBLICATIONS

Kohen, et al. "Antioxidant activity of carnosine, homocarnosine, and anserine present in muscle and brain." Proc Natl Acad Sci USA (1988) 85(9) pp. 3175-3179.
Online-Medical Dictionary "Amino acid" http://cancerweb.ncl.ac.uk/cgi-bin/omd?query=amino+acid. (1997).
Nagai, K., et al. "Realization of Spontaneous Healing Function by Carnosine." Meth and Find Exptl. Clin Pharmacol (1988) vol. 10, No. 8, pp. 497-507.
Tan, K.M.L., et al. "Carnosine and anserine as modulators of neutrophil function." Clin Lab. Haem (1998) Vojl. 20, pp. 239-244.
"New Food Industry" (2001) vol. 43, No. 9, pp. 15-20.
Huang, Su-Ching, et al. "Concentrations and Antioxidative Activity of Anserine and Carnosine in Poultry Meat Extracts Treated with Demineralization and Papain." Proc. Natl. Sci. Counc. ROC(B) (2000) vol. 24, No. 4, pp. 193-201.
Development of industrial refining and separation technology for Dipeptides (Anserine, Carnosine) form fish boiling juice and functional property. Kazuo Sakai, Yoshihara Matahira, Kazuaki Kikuchi.
Candlish, J.K., et al. "Antioxidants in Food and Chronic Degenerative Diseases" Biomedical and Environmental Sciences (1996) vol. 9, pp. 117-123.

*Primary Examiner*—Jon P Weber
*Assistant Examiner*—Abdel A Mohamed
(74) *Attorney, Agent, or Firm*—Ladas and Parry LLP

(57) ABSTRACT

The present invention relates to a composition comprising an effective amount or an effective amount of one or more dipeptides consisting of histidine or the functional equivalent thereof and alanine or the functional equivalent thereof for reducing uric acid in a subject. The invention also provides a method for the treatment of gout or the amelioration of symptoms related to a high level of uric acid comprising the step of administering or applying the above-mentioned dipeptides to a subject.

9 Claims, No Drawings

COMPOSITION CONTAINING DIPEPTIDE OF HISTIDINE AND ALANINE FOR REDUCING URIC ACID AND METHOD FOR REDUCING URIC ACID USING THE DIPEPTIDE

This application is a divisional of application Ser. No. 10/449,053 filed May 30, 2003 (now abandoned) claims the benefit thereof and incorporates the same by reference.

FIELD OF THE INVENTION

The present invention relates to a composition and a method for reducing uric acid in a subject. In particular, the composition of the invention comprises one or more dipeptides consisting of histidine or the functional equivalent thereof and alanine or the functional equivalent thereof, and the method of the invention comprises the steps of administrating or applying the dipeptide(s) described above to a subject in need of reduction of uric acid.

BACKGROUND OF THE INVENTION

Recently, dipeptides have been a target for intensive studies for their physiological functions in mammals. Most of the studies focus on the antioxidant properties of the dipeptides (Boldyrev AA et. al., Mol Chem Neuropathol 1993 May-June, 19(1-2): 185-92; Huang S C and Kuo J C, Proc Natl Sci Counc Repub China B. 2000 October, 24(4): 193-201; Candlish J K and Das N P, 1996 September, 9(2-3): 117-23; and MacFarlane N et. al., J Mol Cell Cardiol. 1991 November, 23(11): 1205-7), which directly or indirectly relate. to anticancer activities (Nagai K and Suda T, 1988 August, 10(8): 497-507; and Holliday R and McFarland G A, Br J Cancer 1996 April, 73(8):966-71), immunity enhancement (Boldyrev A A and Severin S E, Adv Enzyme Regul, 1990, 30:175-94), fat reduction (Chan WK et. al., 1994- July, 29(7):461-6), wound healing improvement (Nagai K and Suda T, 1988 August;10(8):497-507), etc. Carnosine is a dipeptide composed of histidine and alanine. Anserine is a dipeptide found in muscle and formed by a peptide bond between alanine and methyl-histidine. Carnosine and anserine, two highly related compounds, have been indicated for the activities and properties described above by many researchers. In addition, carnosine and anserine have also been shown to have the activities of increasing the speed of cell mitosis through stimulation of neutrophils, thus potentially strengthening the repairing. mechanism of muscle tissues under stress (Tan K M and Candlish J K, 1998 August, 20(4): 239-44).

With these functions in mind, recent studies in fatigue relieve have led to the development and commercialization of a highly concentrated anserine derived from marine sources that could reduce the content of muscular lactic acid and the level of carnitine phosphokinase, and effectively increase the stress-endurance level of muscle (Kazuo Sakai et. al., 2000, "Development of Industrial Refning and Separation Technology for Dipeptides, Anserine and Carnosine, from Fish Boiling Juice and Their Functional Property." Yaizu Suisan Chemical Co., Ltd.). Anserine and carnosine, being highly stable dipeptides, remain intact under low pH (<3.0), and resist against digestion by peptidase and proteases excreted from pancreas or other digestive organs. The dipeptides would find their way through the intestinal membranes, enter blood stream intact, and exert their function directly upon target organs such as liver, kidney and heart. Other dipeptides, such as carcinine, homocarnosine and ophidine, having simi-lar structures to anserine and carnosine are naturally occurring or can be artificially synthesized.

A high level of uric acid may induce gout with symptoms such as muscle spasm, localized swelling, inflammation, joint pains, muscle fatigue, stress feelings and myocardial infraction. Many commercialized drugs have been used to treat gout, such as Benzbromarone (URINORM), Probenecid, Allopurinol, Bucolome, Cinchophan and Colchicine. These drugs work by inhibiting the formation of uric acid, removing the extra uric acid from the body, acting on the kidneys to help the body to eliminate uric acid, inhibiting the activity of xanthine oxidase for the conversion xanthine to uric acid, and accelerating the excretion of uric acid from the body. However, these uricosuric agents simultaneously exhibit a number of side effects such as urinary calculus, gastrointestinal obstruction, jaundice and anemia. Therefore, while there are numerous agents for treating gout, there is still a need for a new drug or a dietary supplement for reducing the level of uric acid and thereby treating gout and moderating gout-related symptoms.

SUMMARY OF THE INVENTION

One object of the invention is to provide a composition for reducing uric acid in a subject comprising an effective amount of one or more dipeptides consisting of histidine or the functional equivalent thereof and alanine or the functional equivalent thereof. The composition. of the invention can be used as a medicament for use in the treatment of gout and related symptoms or in the amelioration of symptoms related to a high level of uric acid, or as a dietary supplement.

Another object of the invention is to provide a method of reducing uric acid in a subject in need thereof, comprising the step of administering or applying an effective amount of one or more dipeptides of the invention to the subject. The method of the invention is useful in the treatment of gout or the amelioration of symptoms related to a high level of uric acid such as muscle spasm, localized swelling, inflammation, joint pains, muscle fatigue, stress feelings, and myocardial infarction.

DETAILED DESCRIPTION OF THE INVENTION

The invention relates to the novel use of the dipeptide composed of histidine or the functional equivalent thereof and alanine or the functional equivalent thereof for reducing uric acid in a subject. In the first aspect, the invention provides a composition comprising an effective amount of one or more dipeptides consisting of histidine or the functional equivalent thereof and alanine or the functional equivalent thereof for reducing uric acid in a subject.

The chemical structures of alanine and histidine are illustrated as follows:

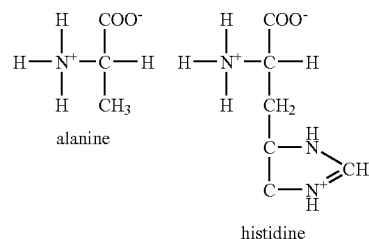

The term "effective amount" of the dipeptide according to the invention used herein refers to an amount of the dipeptide applied to a subject leading to a substantial reduction of uric acid in the subject. The term "dipeptide" used herein refers to a peptide that is composed of two amino acid molecules or the functional equivalents thereof linked by a peptide bond. The term "functional equivalent" of an amino acid refers to a compound modified from the amino acid (e.g., an amino acid substituted by one or more substituents) and having a function substantially equivalent to that of the unmodified amino acid. In one embodiment of the invention, the functional equivalent of histidine is methylhistidine or histamine and the functional equivalent of alanine is γ-aminobutyric acid. The dipeptide of the invention can be naturally occurring or artificially synthesized. Examples of the dipeptides for use in the invention include, but are not limited to, carnosine (β-alanyl-L-histidine), anserine (β-alanyl-1-methyl-L-histidine), carcinine (beta-alanylhistamine), homocarnosine (γ-aminobutyryl-L-histidine) and ophidine (β-alanyl-L-3-methylhistidine), which are commercially available.

Preferably, the composition of the invention comprises two or more dipeptides according to the invention. More preferably, the composition of the invention comprises carnosine and anserine. Carnosine and anserine may comprise about 5-30% w/w and about 95-70% w/w of the total amount of the dipeptides, respectively Preferably, the composition of the invention comprises, on the basis of the total amount of the dipeptides, about 7% w/w of carnosine and about 90% w/w of anserine.

The composition of the invention can further comprise oligopeptides, free amino acids, carnitine and a pharmaceutically or physiologically acceptable excipient. Suitable pharmaceutically acceptable excipients comprises, but are not limited to, dextrin, lactose, starch, talc, stearic acid, tartaric acid, alcohol, glycerin, vegetable oils and waxes.

To be used as a medicament, the composition of the invention can be prepared in appropriate pharmaceutical dosage forms, e.g., tablets, powders, granules, capsules, liquid and suspension, (for use via different administration routes) by conventional methods with proper pharmaceutically acceptable excipients.

As a medicament, the composition of the invention may be administered through any suitable routes, such as oral or parenteral route. The dosage of the composition will vary with the species of the dipeptide, the route of administration and the conditions of the subject to be treated, which can be readily determined by skilled physicians. For oral administration, for instance, the composition of the invention is administered to provide an amount of about 8 mg to about 50 mg, preferably about 10 mg to about 45 mg, of the dipeptide per day.

The composition of the invention, when used as a medicament, is useful in reducing uric acid in a subject, such as a mammal, preferably, a human. In particular, the composition of the invention is useful in controlling the level of uric acid in a subject suffering from gout and ameliorating symptoms related to a high level of uric acid such as muscle spasm, localized swelling, inflammation, joint pains, muscle fatigue, stress feelings, and myocardial infraction.

For used as a dietary supplement, the composition of the invention can be formulated in a suitable form for oral application, such as tablets, powders, granules, capsules, liquid and suspensions by conventional methods. The dosage of the dietary supplement will vary with the species of the dipeptide and the conditions of the subject to which the dietary supplement is applied. Preferably, the dietary supplement of the invention is applied to provide an amount of about 8 mg to about 50 mg, preferably about 10 mg to about 45 mg, of the dipeptide per day.

Many uricosuric agents known for the treatment of gout, such as Benzbromarone (URINORM), Probenecid, Allopurinol, Bucolome, Cinchophan and Colchicine, are commercially available. The composition of the invention can be used in combination with one or more uricosuric agents described above for reducing uric acid. When a combination use is desired, the composition of the invention and the one or more uricosuric agents can be administered or applied sequentially or simultaneously. For instance, the composition of the invention may further comprise one or more uricosuric agents in a single dosage form. Alternatively, the composition of the invention and the one or more uricosuric agents are formulated as separate dosage forms and administrated or applied simultaneously or sequentially to a subject.

In another aspect, the invention provides a method for reducing uric acid in a subject in need thereof, comprising the step of administering or applying to the subject an effective amount of one or more dipeptides consisting of histidine or the functional equivalent thereof and alanine or the functional equivalent thereof. Preferably, the method of the invention comprising the step of administering or applying to the subject the composition according to the invention.

In particular, the method of the invention is useful in the treatment of gout or the amelioration of symptoms related to a high level of uric acid such as muscle spasm, localized swelling, inflammation, joint pains, muscle fatigue, stress feelings, and myocardial infarction. The terms "effective amount," "dipeptide" and "functional equivalent" used herein are as defined above. Preferably, two or more dipeptides according to the invention of proper ratios are administered into a subject in need of reduction of uric acid. More preferably, about 5-30% w/w of carnosine and about 95-70% w/w of anserine, most preferably, about 7% w/w of carnosme and about 90% w/w of anserine, on the basis of the total amount of the two dipeptides, are administered.

The dipeptide of the invention can be administered or applied to a subject by way of any suitable routes such as oral or parenteral route. The effective amount of the one or more dipeptides for treating a subject with an abnormal level of uric acid varies in accordance with the species of the dipeptide, the route of administration and application and the conditions of the subject to be treated, which can be readily determined by skilled physicians. For an oral administration or application, for instance, the dipeptide may be administered to a subject in an amount of about 8 mg to about 50 mg, preferably about 10 to about 45 mg per day.

In one embodiment of the invention, the dipeptide of the invention is administered or applied in combination with one or more conventional uricosuric agents such as Benzbromarone (URINORM), Probenecid, Allopurinol, Bucolome, Cinchophan and Colchicine. When a combined administration or application is desired, the dipeptide of the invention and the one or more uricosuric agents can be administered or applied sequentially or simultaneously. For instance, the dipeptide of the invention may be formulated with the one or more uricosuric agents in a single dosage form. Alternatively, the dipeptide of the invention and the one or more uricosuric agents are formulated as separate dosage forms and administered or applied simultaneously or sequentially to a subject in need thereof.

EXAMPLES

The present invention will become apparent with reference to the examples below. The examples described below are given by way of illustration only and are not intended to be any limitation to the present invention.

Example 1

Anserine powder with the trade name "Marine Active" (Yaizu Suisan Kagaku Kaisha, Yaizu, Shizuoka prefecture, Japan) containing 5 % w/w of a dipeptide mixture (90.9% of anserine and 7.3% of carnosine), 15% w/w of oligopeptides developed from an enzymatic digestion of fish protein, 10% w/w of free amino acids, and 70% w/w of dextrin was filled into gelatin capsules at 250 mg each. A gout patient with a high level of uric acid in serum consumed one capsule before each meal during a period of 24 hours. The level of uric acid in serum was monitored by UroSpeed, a rapid sero-uric acid test strip (Apex Biotechnology Co., Inc. Hsinchu, Taiwan, ROC). The results are shown in Table 1.

TABLE 1

Influence on the level of uric acid in serum by Marine Active

| Day | time | Dosage | Uric acid mg/dl | Note |
|---|---|---|---|---|
| Day 1 | 8:30 | 250 mg | 13.4 | Gout syndromes developed, such as swelling in right ankle with pain at the previous night |
| | 9:50 | 0 | 10.4 | |
| | 12:00 | 250 mg | 9.1 | Pain disappears |
| | 18:00 | 250 mg | 8.5 | |
| | 21:00 | 0 | 7.4 | |
| Day 2 | 8:30 | 0 | 10.1 | |

As shown in Table 1, the level of uric acid in serum of the patient was significantly reduced after consuming the Marine Active. Specifically, after consuming 250 mg of the Marine Active at eight thirty o'clock in the morning, the pain resulted from the swelling ankle of the patient disappeared. However, when the patient stopped consuming the Marine Active at the second day, the level of uric acid in serum of the patient returned to a level as high as 10.1 mg/dl. Fortunately; the gout symptoms did not resume and remained the same for another three weeks. The patient felt another onset of preliminary symptom of gout at the end of the third week and started taking Marine Active 250 mg capsules. Four hours later, the symptom disappeared again.

Example 2

Eight patients (labeled with the symbols of "XL," "CH," "HT," "HH," "LH," "CP," "CD" and "CC," respectively) having chronic hyperserouric content (>7.5 ppm) was taken off the regular medication for at least 3 days and the average level of uric acid in serum thus increased to more than 8.5 mg/dl. One Marine Active capsule of 250 mg was consumed before each meal, and it was found that the level of uric acid in serum of the patients decreased to 7.5 mg/dl at average. In addition, the symptoms associated with gout of the patients, such as pain, sore, inflammation, muscle fatigue and stress feelings were also significantly reduced. This is quite unexpected and deemed extraordinary. The detailed results are shown in Table 2.

TABLE 2

Influence on uric acid level in serum by Marine Active

| Patient | Age | Uric acid (mg/dl) before taking Marine Active | Uric acid (mg/dl) 7 days after taking Marine Active |
|---|---|---|---|
| XL | 40 | 10.5 | 7.0 |
| CH | 35 | 9.6 | 6.5 |
| HT | 60 | 12.5 | 7.2 |
| HH | 58 | 10.0 | 7.3 |
| LH | 34 | 8.8 | 7.0 |
| CP | 42 | 9.8 | 6.8 |
| CD | 38 | 8.9 | 6.3 |
| CC | 55 | 12.3 | 8.5 |

What is claimed is:

1. A method for reducing uric acid in a subject in need thereof, comprising the step of administering or applying to the subject a composition comprising an effective amount of anserine and a pharmaceutically acceptable excipient.

2. The method of claim 1, wherein the composition is administered or applied to the subject for the treatment of gout or the amelioration of symptoms related to a high level of uric acid selected from the group consisting of muscle spasm, localized swelling, inflammation, joint pains, muscle fatigue, stress and myocardial infarction.

3. The method of claim 1, wherein the pharmaceutically acceptable excipient is selected from the group consisting of dextrin, lactose, starch, talc, stearic acid, tartaric acid, alcohol, glycerin, vegetable oils and waxes.

4. The method of claim 1, wherein the pharmaceutically acceptable excipient is dextrin.

5. The method of claim 1, wherein the composition is administered to the subject in a capsule.

6. The method of claim 1, wherein the composition is administered or applied in combination with a uricosuric agent, simultaneously or sequentially.

7. The method of claim 6, wherein the uricosuric agent is selected from the group consisting of (3,5-dibromo-4-hydroxy-phenyl)-(2-ethylbenzofuran-3-yl) methanone, 4-(dipropylsulfamoyl)benzoic acid, 2,4,8,9-tetrazabicyclo[4.3.0]nona-1,3,6-trien-5-one, 5-butyl-1-cyclohexyl-1,3-diazinane-2,4,6-trione, 2-phenylquinoline-4-carboxylic acid, and N-[(7S)-5,6,7,9-tetrahydro-1,2,3,10-tetramethoxy-9-oxobenzo[a]heptalen-7-yl]-acetamide.

8. The method of claim 1, wherein the composition further comprises an oligopeptide, free amino acids, carnosine and carnitine.

9. The method of claim 8, wherein the oligopeptide comprises at least one dipeptide consisting of a first amino acid selected from the group consisting of histidine, methylhistidine and histamine and a second amino acid selected from the group consisting of alanine and γ-aminobutyric acid.

* * * * *